(12) United States Patent
Takayanagi et al.

(10) Patent No.: US 9,492,684 B2
(45) Date of Patent: Nov. 15, 2016

(54) PARTICLE THERAPY SYSTEM

(71) Applicant: HITACHI, LTD., Tokyo (JP)

(72) Inventors: Taisuke Takayanagi, Tokyo (JP); Koji Matsuda, Tokyo (JP);
(Continued)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/763,595

(22) PCT Filed: Oct. 10, 2013

(86) PCT No.: PCT/JP2013/077640
§ 371 (c)(1),
(2) Date: Jul. 27, 2015

(87) PCT Pub. No.: WO2014/119050
PCT Pub. Date: Aug. 7, 2014

(65) Prior Publication Data
US 2015/0352372 A1 Dec. 10, 2015

(30) Foreign Application Priority Data
Jan. 29, 2013 (JP) .................................. 2013-014153

(51) Int. Cl.
*A61N 5/10* (2006.01)

(52) U.S. Cl.
CPC .............. *A61N 5/1043* (2013.01); *A61N 5/10* (2013.01); *A61N 5/1031* (2013.01);
(Continued)

(58) Field of Classification Search
CPC ................ A61N 5/1031; A61N 5/1043; A61N 5/1075; A61N 5/1045; A61N 2005/1043; A61N 2005/1081
See application file for complete search history.

(56) References Cited

U.S. PATENT DOCUMENTS 6,080,992 A 6/2000 Nonaka et al.
8,735,848 B2 * 5/2014 Asaba .................. A61N 5/1031
250/396 R
(Continued)

FOREIGN PATENT DOCUMENTS

JP 10-234874 A 9/1998
JP 11-47291 A 2/1999
(Continued)

OTHER PUBLICATIONS

International Preliminary Report on Patentability received in corresponding International Application No. PCT/JP2013/077640 dated Aug. 13, 2015.
(Continued)

*Primary Examiner* — David Porta
*Assistant Examiner* — Faye Boosalis
(74) *Attorney, Agent, or Firm* — Mattingly & Malur, PC

(57) ABSTRACT

The present invention provides a particle therapy system including an irradiation compensating device made up of an energy absorber, a first collimator, and a second collimator for use in a short-range region. The irradiation compensating device is characterized by a mechanism for attaching and detaching the first energy absorber, first collimator, and second collimator. The first collimator is located upstream where the beam diameter is small with a view to suppressing the width of the compensating device, thereby contributing to making the compensating device small and lightweight. The second collimator is located downstream to improve penumbrae.

12 Claims, 16 Drawing Sheets

COLLIMATORS A AND B (FULLY CLOSED) FOR SHORT-RANGE APPLICATOR (FOR HEAD AND NECK AREA) AS VIEWED FROM THE DOWNSTREAM SIDE

COLLIMATOR A FOR SHORT-RANGE APPLICATOR (FOR SPINE) AS VIEWED FROM THE DOWNSTREAM SIDE

COLLIMATOR A FOR SHORT-RANGE APPLICATOR (FOR GENERAL PURPOSE) AS VIEWED FROM THE DOWNSTREAM SIDE

(72) Inventors: Ryosuke Shinagawa, Tokyo (JP);
Chihiro Nakashima, Tokyo (JP); Arao Nishimura, Tokyo (JP); Hiroki Shirato, Sapporo (JP); Taeko Matsuura, Sapporo (JP); Shinichi Shimizu, Sapporo (JP); Rikiya Onimaru, Sapporo (JP); Kikuo Umegaki, Sapporo (JP)

(52) U.S. Cl.
CPC ........... *A61N 5/1045* (2013.01); *A61N 5/1065* (2013.01); *A61N 5/1077* (2013.01); *A61N 2005/1087* (2013.01); *A61N 2005/1095* (2013.01)

(56) References Cited

U.S. PATENT DOCUMENTS

2008/0023644 A1   1/2008   Pedroni

2009/0242789 A1   10/2009  Tachikawa

FOREIGN PATENT DOCUMENTS

| JP | 2002-306617 A | 10/2002 |
| JP | 2007-534391 A | 11/2007 |
| JP | 2009-236867 A | 10/2009 |
| JP | 2010-29594 A  | 2/2010  |

OTHER PUBLICATIONS

Uwe Titt et al., Adjustment of the lateral and longitudinal size of scanned proton beam spot using a pre-absorber to optimize penumbrae and delivery efficiency, Physics and Engineering of Medicine, Dec. 2010; 55(23): 7097-7106.

M. Bues et al., Therapeutic step and shoot proton beam spot-scanning with a multi-leaf collimator: a monte carlo study, Radiation Protection Dosimetry 2005, pp. 164-169, vol. 115, No. 1-4.

International Search Report of PCT/JP2013/077640.

* cited by examiner

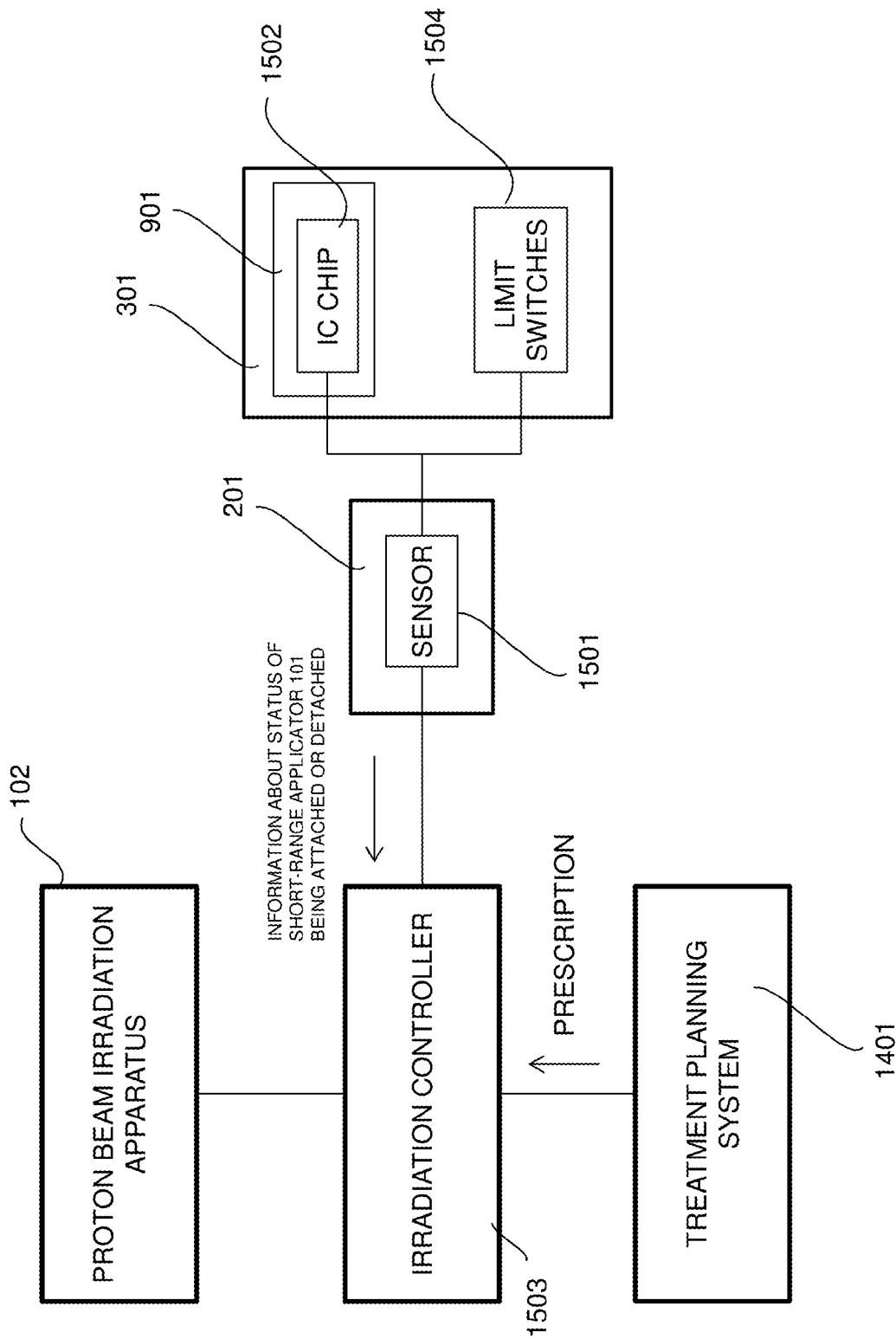

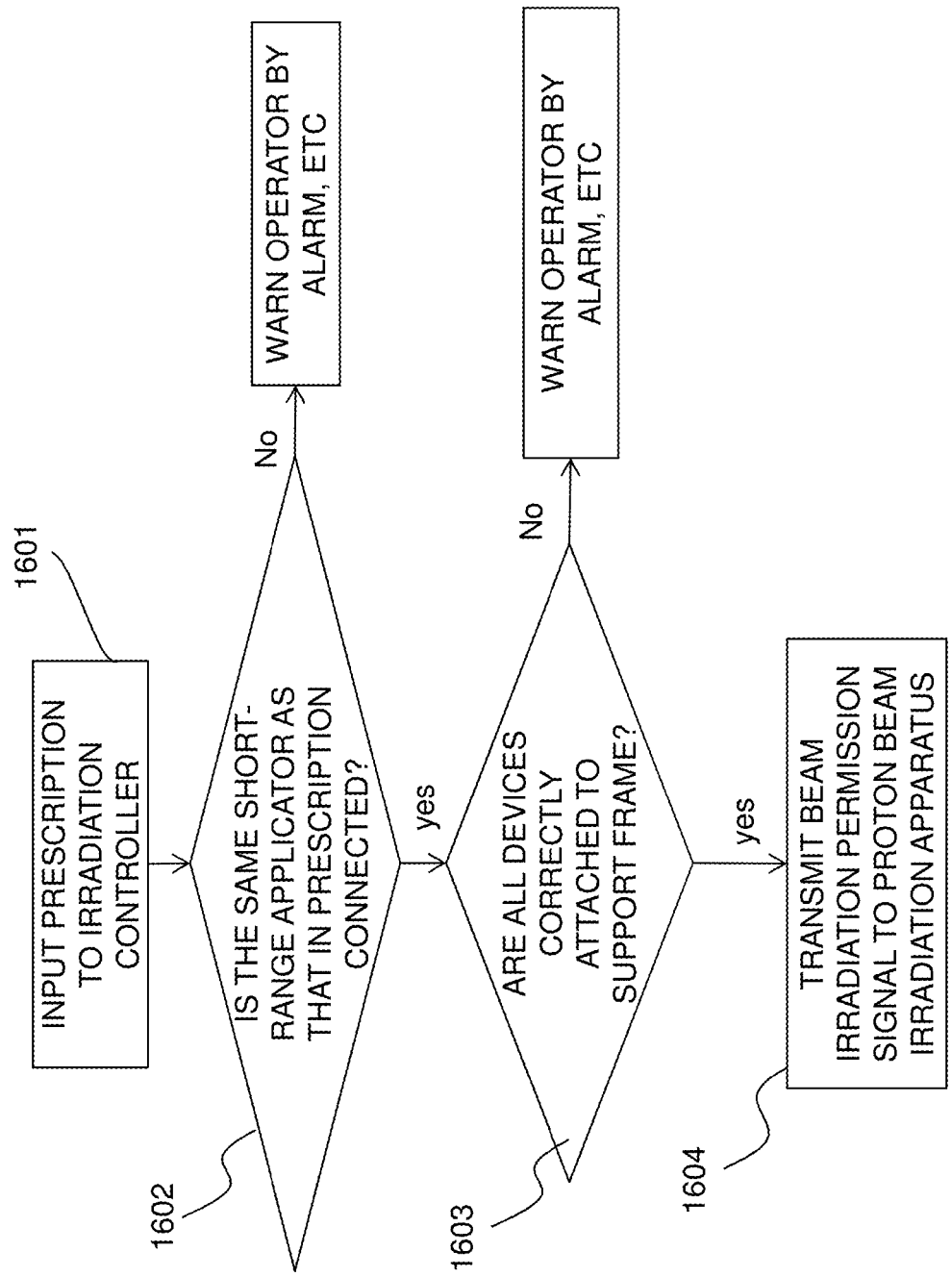

PARTICLE THERAPY SYSTEM

TECHNICAL FIELD

The present invention relates to a particle therapy system.

BACKGROUND ART

In particle therapy, the scanning method has been gaining widespread acceptance. The scanning method involves dividing a target into minute regions (called spots hereunder) and irradiating each spot with a small-diameter beam. When a spot has been irradiated with a predetermined dose, the irradiation with the beam is stopped and the beam is moved to scan the next spot. Where the beam is to be moved for scanning in a direction (lateral direction) perpendicular to the beam advancing direction (depth direction), a scanning magnet is used. When all spots at a given depth have been irradiated with the predetermined dose, the beam is moved for scanning in the depth direction. Where the beam is to be moved for scanning in the depth direction, the energy of the beam is changed by an accelerator or by a range shifter. Eventually, all spots (i.e., the entire target) are irradiated with a uniform amount of dose.

The beam for each spot has a two-dimensional Gaussian distribution in the lateral direction. On the isocenter plane, $1\sigma$ is about 3 to 20 mm; the value is smaller the higher the beam energy. A low-energy beam has a large angular divergence per unit distance due to multiple coulomb scattering. The beam increases in diameter as it passes through an irradiation nozzle.

Thus the low-energy beam is used to form the dose distribution for the target located at a shallow position (called the short-range region) from the surface of the irradiated body. This tends to increase penumbrae. Outside the target or in a region near the boundary between the target and the normal tissue, penumbrae represent the lateral distance over which the irradiation dose drops from 80% to 20% and have positive correlation with the beam diameter. It is assumed here that the irradiation dose near the target center is 100%. The smaller the penumbrae, the more accurate the dose distribution is in conformance with the shape of the target.

Given that problem, Non-Patent Document 1 proposes a technique that involves setting up an energy absorber upstream of the irradiated body. According to this technique, a high-energy beam is emitted to the target in the short-range region and is reduced in energy by the energy absorber immediately before entering the irradiated body. Because the drift distance of the beam in the low-energy state is suppressed, the beam diameter can be reduced and the penumbrae improved. Meanwhile, Non-Patent Document 2 proposes a technique involving the use of a collimator to block the beam that is incident outside the target, thereby improving the penumbrae.

PRIOR ART DOCUMENTS

Non-Patent Documents

Non-Patent Document 1: U. Titt, et al., "Adjustment of the lateral and longitudinal size of scanned proton beam spot using a pre-absorber to optimize penumbrae and delivery efficiency," Phys. Med Biol. 55(2010) 7097-7106.

Non-Patent Document 2: M. Bues, et al., "Therapeutic step and shoot proton beam spot-scanning with a multi-leaf collimator: a monte carlo study," Radiat. Prot. Dosim. 115 164-9.

SUMMARY OF THE INVENTION

Problem to be Solved by the Invention

Using both the energy absorber of Non-Patent Document 1 and the collimator of Non-Patent Document 2 can conceivably further improve penumbrae for scanning irradiation in the short-range region. However, there have been problems with how to attach and detach these two devices to and from the irradiation nozzle. For the target at a deep position from the surface of the irradiated body, i.e., outside the short-range region, these two devices are not used. This requires excluding the position from the region passed by the beam.

Where an energy absorber driving device and a multileaf collimator are installed in the irradiation nozzle, the devices are automatically attached and detached so that the burden on the operator is alleviated. However, since the irradiation nozzle becomes larger in size in the depth direction, the drift distance of the beam inside the irradiation nozzle increases and so does the beam diameter under high-energy conditions. This means that although penumbrae can be improved in the irradiation of the short-range region thanks to the workings of the energy absorber and collimator, the irradiation outside the short-range region will conversely increase the penumbrae. Furthermore, with the irradiation nozzle getting larger in size, the rotating gantry has increased in size and so has the cost of the particle therapy system.

Where the tip of the irradiation nozzle is equipped with applicator fittings for manual attachment and detachment of an applicator by the operator, these problems can be solved. Here, the applicator refers to an irradiation compensating device composed of an energy absorber and a collimator and used in the short-range region. However, the irradiation nozzle that forms an irradiation field using the scanning method is generally capable of scanning with the beam within a range of 400 mm by 300 mm in the lateral direction, so that the applicator complying with such specifications can be large and heavy. This means that manually attaching and detaching the applicator to and from the irradiation nozzle can be a significant burden on the operator.

An object of the present invention is to provide a particle therapy system equipped with an irradiation nozzle that forms the irradiation field using the scanning method in a manner improving the penumbrae in the short-range region without hiking costs, increasing the penumbrae outside the short-range region, or increasing the burden on the operator.

Means for Solving the Problem

To solve the problem outlined above, the present invention provides a particle therapy system including: an irradiation nozzle forming an irradiation field using a scanning method; and an irradiation compensating device used in a short-range region, the irradiation compensating device having an energy absorber, a first collimator, a second collimator, and a mechanism for attaching and detaching the energy absorber, the first collimator, and the second collimator. The irradiation nozzle has a mechanism for attaching and detaching the irradiation compensating device.

Effect of the Invention

The present invention thus provides the particle therapy system having the irradiation nozzle forming the irradiation field using the scanning method, without hiking costs, increasing the penumbrae outside the short-range region, or increasing the burden on the operator.

BRIEF DESCRIPTION OF THE DRAWINGS

FIG. 15 is a block diagram of an interlock mechanism used in conjunction with the short-range applicator as part of the embodiment of the invention; and FIG. 16 is a flowchart showing the workings of the interlock mechanism used in conjunction with the short-range applicator as part of the embodiment of the invention.

MODES FOR CARRYING OUT THE INVENTION

Figure 1:
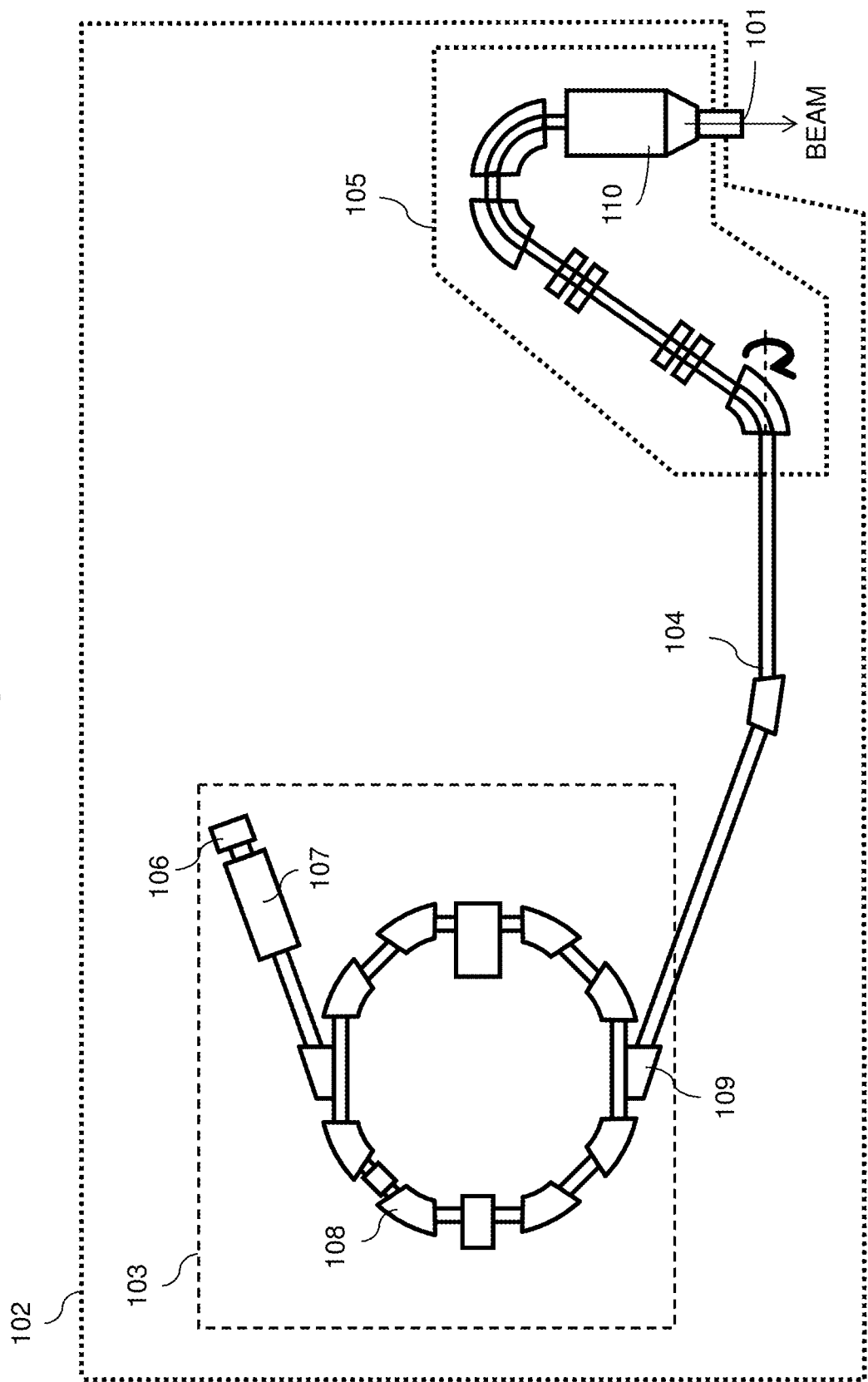
FIG. 1 is a block diagram showing an overall configuration of a particle therapy system as one embodiment of the present invention.

The structures and the workings of the particle therapy system as one embodiment of the present invention are explained below by use of FIGS. 1 through 16. FIG. 1 is a block diagram showing an overall configuration of the particle therapy system as the embodiment of the invention. The particle therapy system includes an irradiation compensating device for the short-range region (called the short-range applicator) 101 and a proton beam irradiation apparatus 102. Although the proton beam irradiation apparatus 102 is used here as an example in explaining this embodiment, the present invention can also apply to heavy particle beam irradiation apparatuses that use particles having a mass heavier than protons (e.g., carbon ion beam).

As shown in FIG. 1, the proton beam irradiation apparatus 102 includes a proton beam generator 103, a proton beam transfer 104, and a rotating irradiation system 105. Although the rotating irradiation system 105 equipped with a rotating gantry is used here as an example in explaining this embodiment, a fixed irradiation system may be adopted instead.

The proton beam generator 103 includes an ion source 106, a preaccelerator 107 (e.g., linear accelerator), and a synchrotron 108. Proton ions generated by the ion source 106 are first accelerated by the preaccelerator 107. The proton beam (called the beam hereunder) extracted from the preaccelerator 107 is accelerated by the synchrotron 108 up to a predetermined energy level before being extracted from an extraction deflector 109 to the proton beam transfer 104. Eventually, the beam is emitted to the irradiated body via the rotating irradiation system 105. The rotating irradiation system 105 has a rotating gantry (not shown) and an irradiation nozzle 110. The irradiation nozzle 110 arranged in the rotating gantry is rotated at the same time as the rotating gantry. The proton beam transfer 104 is partially attached to the rotating gantry. Although the synchrotron 108 is adopted as a proton beam accelerator in this embodiment, a cyclotron or a linear accelerator may be used instead.

Explained next is an outline of the scanning method implemented by the irradiation nozzle 110 of this embodiment. According to the scanning method, the range of irradiation is divided into minute regions (spots), each of which is irradiated with a beam. When a given spot has been irradiated with a predetermined dose, the irradiation is stopped and the beam is moved to scan the next predetermined spot. For scanning with the beam in the lateral direction, a scanning magnet (not shown) attached to the irradiation nozzle is used. When all spots at a given depth have been irradiated with the predetermined dose, the irradiation nozzle 110 moves the beam for scanning in the depth direction. The scanning with the beam in the depth direction is implemented by changing the beam energy through the use of the synchrotron 108 or a range shifter (not shown) attached to the irradiation nozzle or to some other suitable device. The procedure above is repeated until a uniform dose distribution is accomplished.

The dose distribution of the beam per spot in the lateral direction constitutes a Gaussian distribution where $1\sigma=3$ mm to 20 mm on the isocenter plane. With this embodiment, a straight line passed by the beam center when the scanning magnet is not excited is defined as the beam axis. Also, the point of intersection between the beam axis and the rotation axis of the rotating irradiation system 105 is defined as the isocenter.

Figure 2:
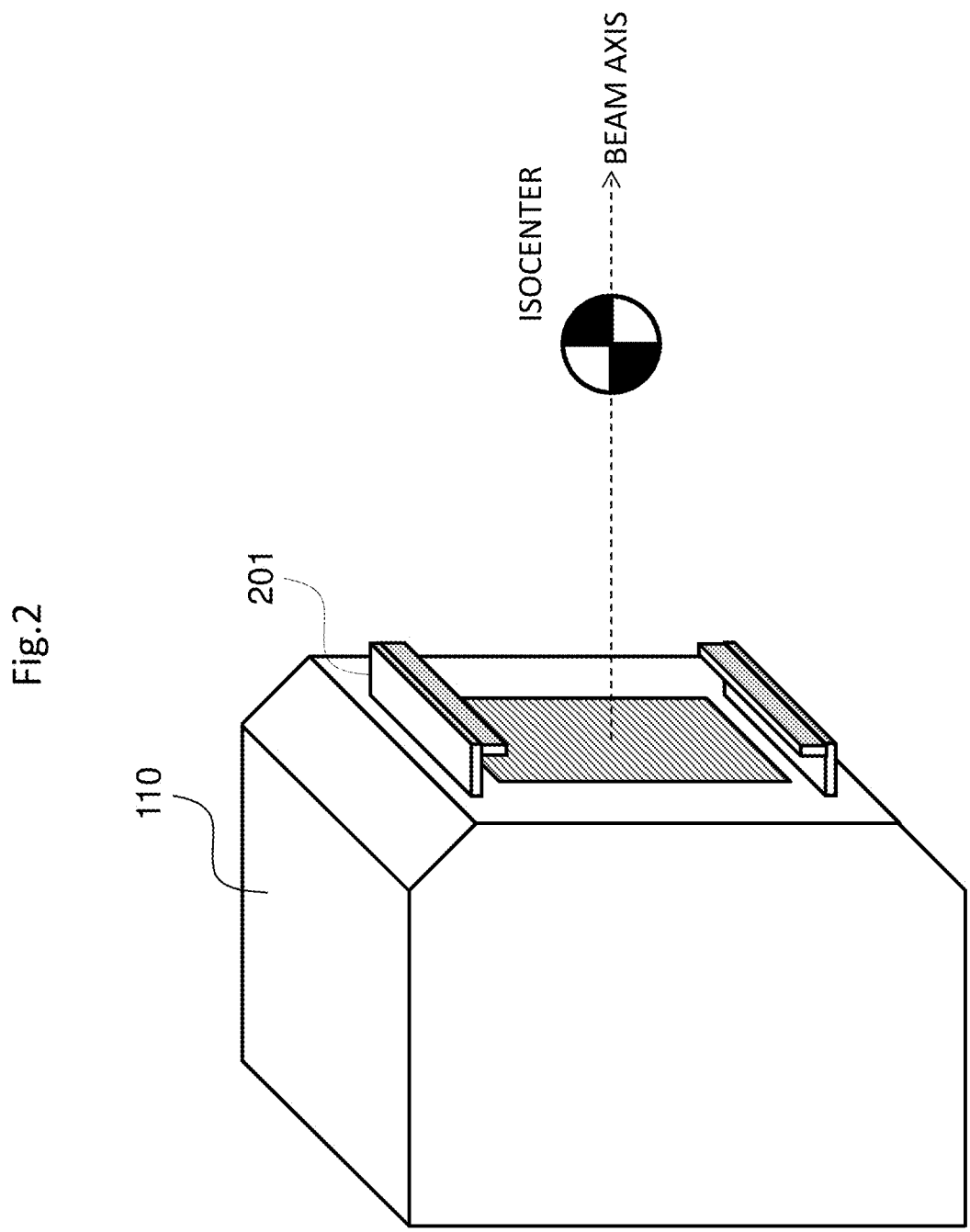
FIG. 2 is a schematic diagram of an irradiation nozzle as part of the embodiment of the invention.

As shown in FIG. 2, the tip of the irradiation nozzle 110 is equipped with a slot C 201 to which the short-range applicator is to be attached.

Figure 3:
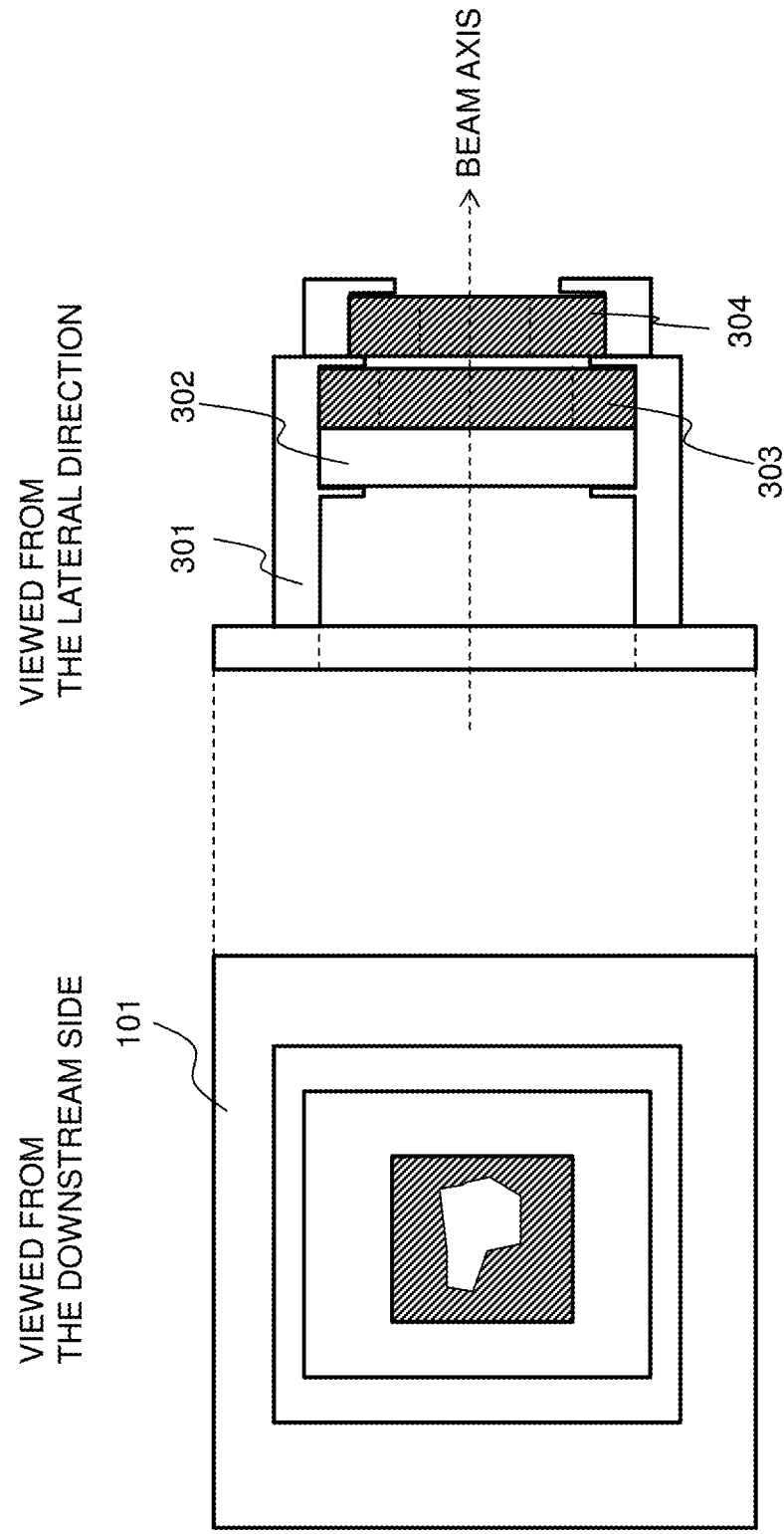
FIG. 3 is a schematic diagram of a short-range applicator as part of the embodiment of the invention.
Figure 4:
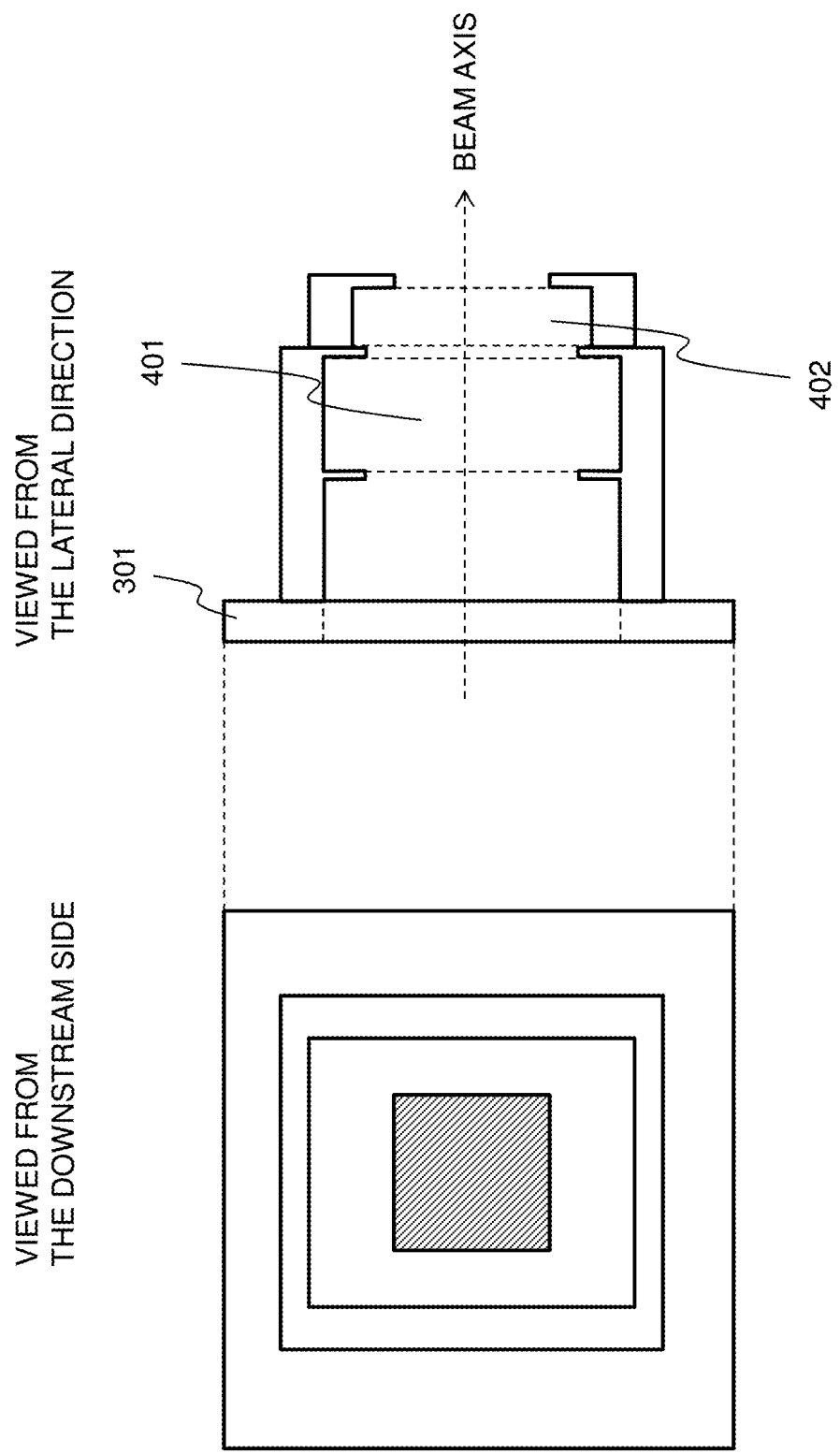
FIG. 4 is a schematic diagram of a support frame as part of the embodiment of the invention.

FIG. 3 is a schematic diagram of the short-range applicator. The short-range applicator 101 is made up of a support frame 301, an energy absorber 302, a first collimator 303 (called the collimator A hereunder), and a second collimator 304 (called the collimator B). The short-range applicator 101 is attached to the irradiation nozzle 110 with a view to improving penumbrae during beam emission to the short-range region. As shown in FIG. 4, the support frame 301 includes a slot A 401 housing the energy absorber 302 and collimator A 303, and a slot B 402 accommodating the collimator B 304.

This embodiment is characterized in that the collimator for the short-range applicator 101 is divided into the collimator A 303 and collimator B 304. To improve penumbrae requires installing the collimator as downstream as possible. However, since the beam diameter increases the more downstream the collimator is located, a laterally extended heavy collimator is needed to shield beam leakage. The above problem is solved by dividing the collimator into two collimators: (a) a collimator (A 303) having the function of shielding beam leakage, and (b) a collimator (B 304) shaping the beam in the lateral direction (i.e., perpendicular to the beam advancing direction) along the target shape and offering the function of improving penumbrae. The collimator A 303 is located upstream where the beam diameter is small in order to reduce the collimator width, contributing to making the short-range applicator 101 small and lightweight. The collimator B 304 is located downstream so as to improve penumbrae. Since the collimator B 304 has no need for the ability to shield beam leakage, it need not be as wide as the collimator A 303, as shown in FIG. 3. Because the divided collimators are structured to be individually attached to the support frame 301, the weight per part is reduced so that the burden on the operator is further alleviated.

Figure 5:
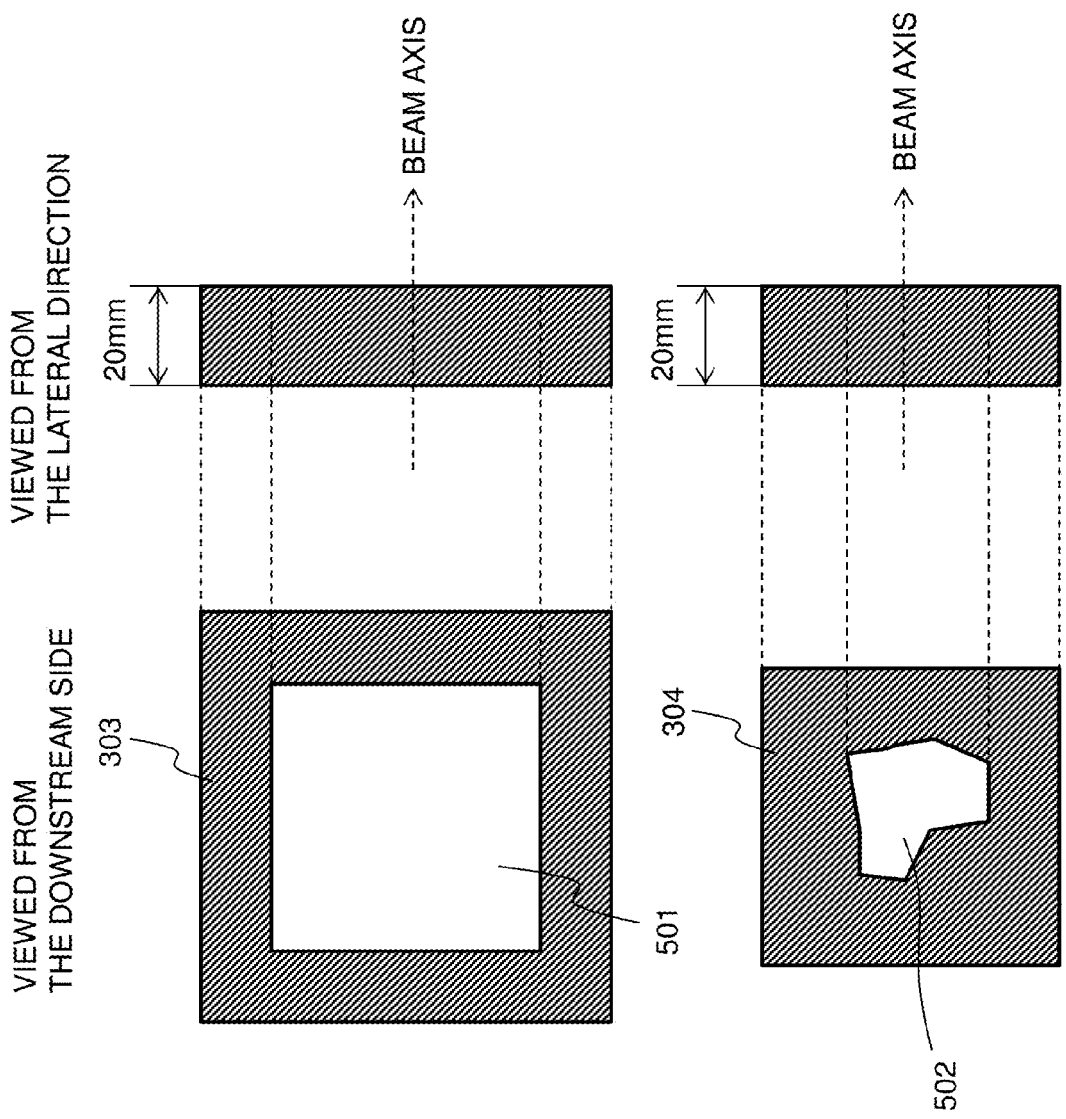
FIG. 5 is a schematic diagram of a collimator A and a collimator B as part of the embodiment of the invention.

The structures of the collimators A 303 and B 304 are explained below by use of FIG. 5. The collimator A uses a brass plate 20 mm thick to shield beam leakage around the irradiation field. An aperture 501 is formed at the center of the collimator A 303 to shield only the beam leaking outside of the irradiation field. The above specification provides sufficient shielding effects for this embodiment because the short-range applicator 101 is used only where regions less than 100 mm of depth are irradiated. However, depending on use conditions, the material and thickness of the collimator A 303 may need to be altered (e.g., the collimator needs to be thicker if the short-range applicator is used to irradiate deeper regions).

As with the collimator A 303, the collimator B 304 uses a brass plate 20 mm thick. The collimator B 304 is used in order to form the beam shape in the lateral direction along the target shape and thereby to improve the penumbrae of the dose distribution. As shown in FIG. 5, the collimator B 304 is provided with an aperture 502 in conformity with the target shape and specific to the patient. As with the collimator A 303, the above specification provides sufficient effects for this embodiment because the short-range applicator 101 is used only where regions less than 100 mm of depth are irradiated. However, depending on use conditions, the material and thickness of the collimator B 304 may need to be altered as well.

Figure 6:
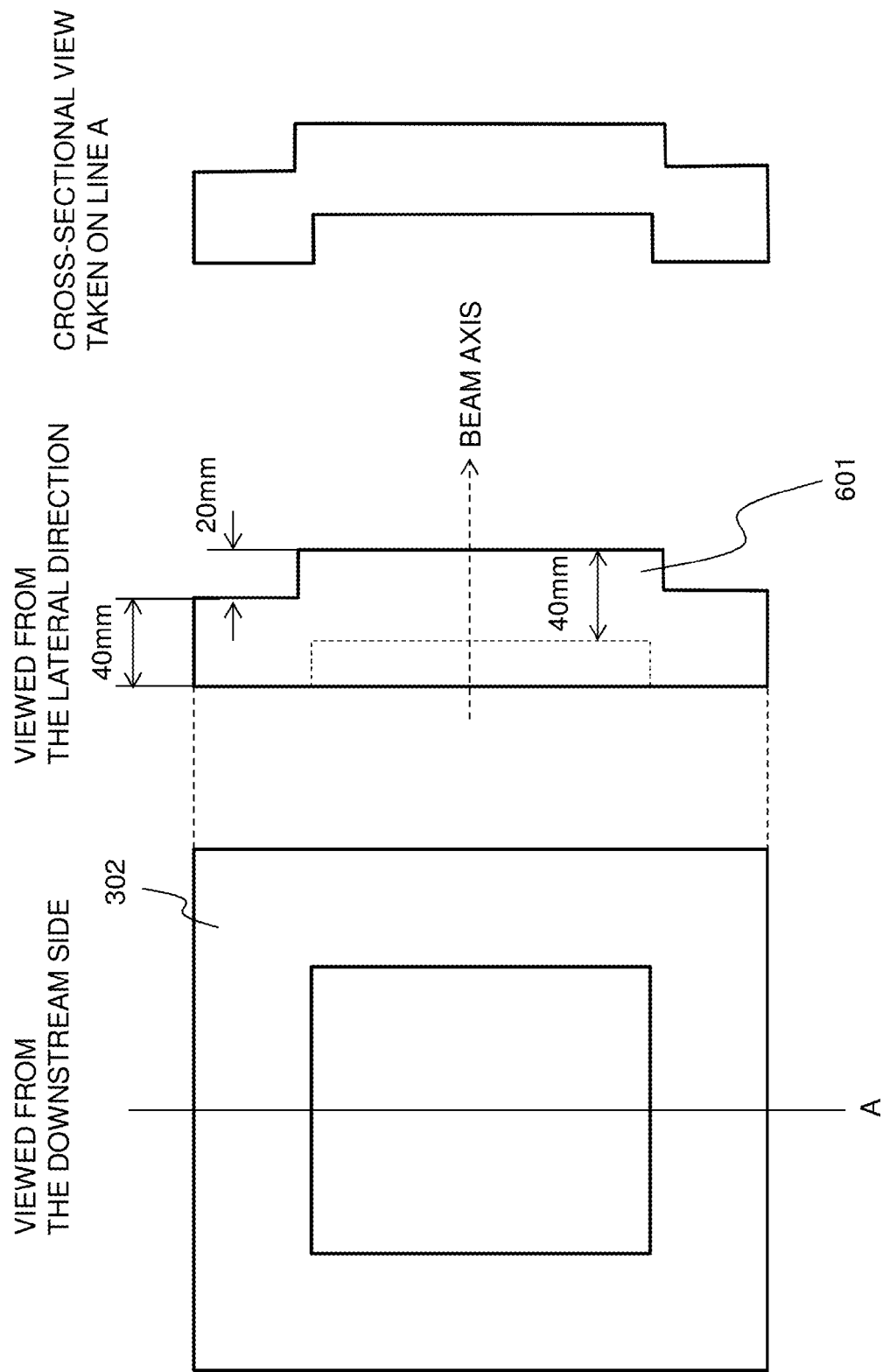
FIG. 6 is a schematic diagram of an energy absorber as part of the embodiment of the invention.
Figure 7:
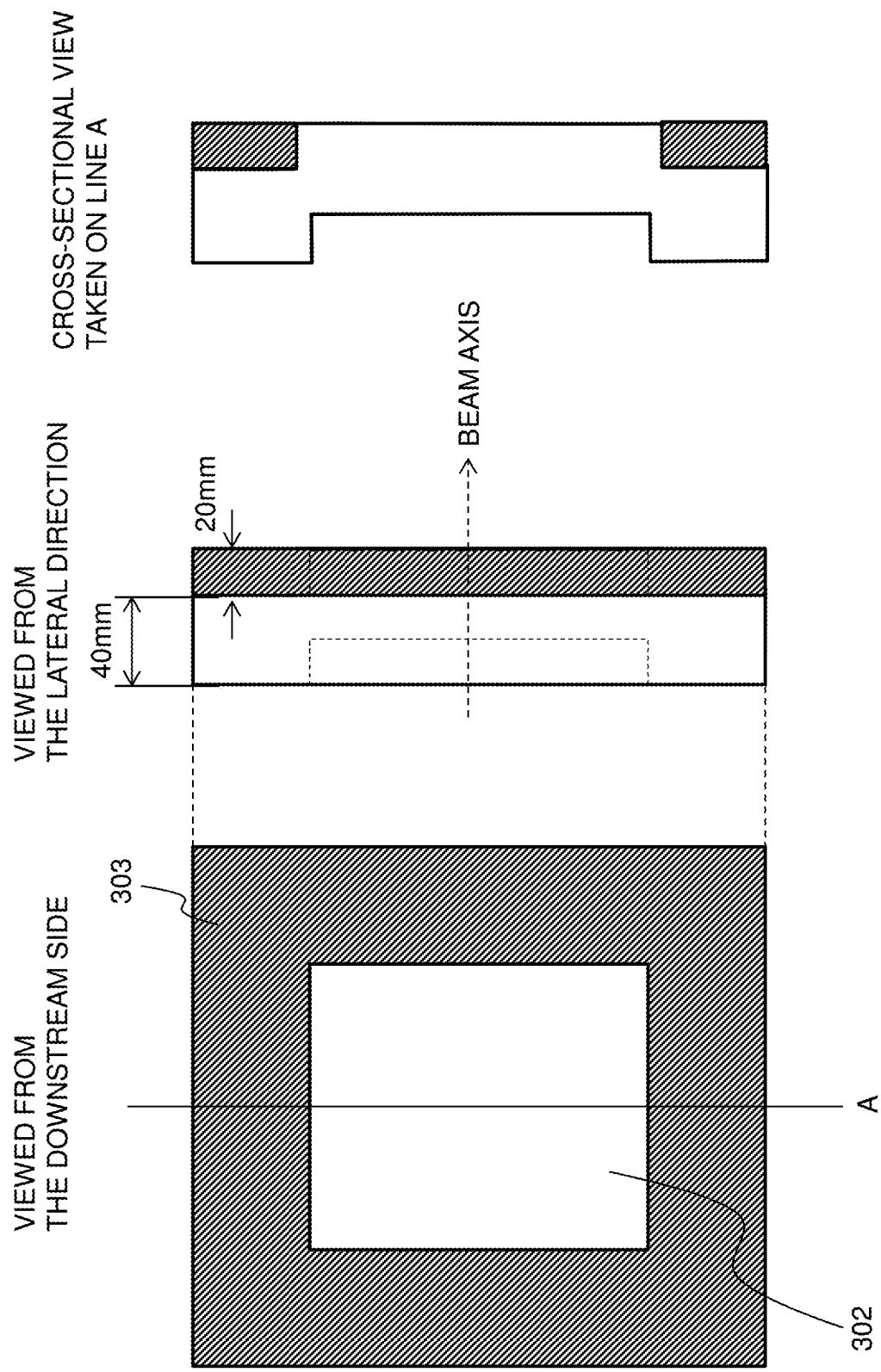
FIG. 7 is a schematic diagram of another energy absorber and another collimator A as part of the embodiment of the invention.
Figure 8:
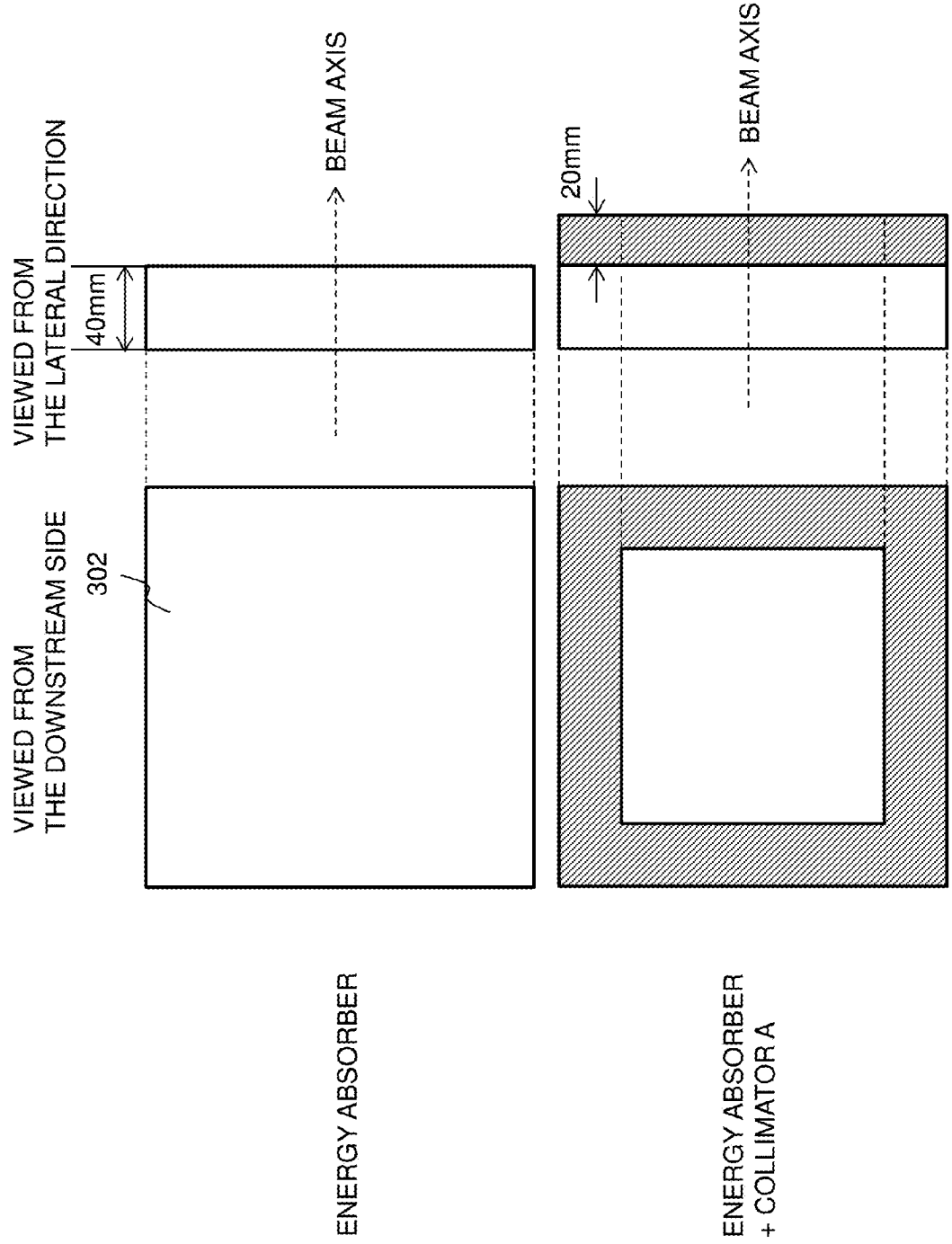
FIG. 8 is a schematic diagram of another energy absorber and another collimator A as part of the embodiment of the invention.

FIG. 6 is a schematic diagram of the energy absorber 302. In this embodiment, an ABS resin with a water equivalent thickness of 40 mm is used as the energy absorber 302. Depending on use conditions, an energy absorber of a different material with a different water equivalent thickness may be used. As shown in FIG. 6, the energy absorber 302 of this embodiment has its center portion protruding in the downstream direction (i.e., there is a central protrusion 601). With this structure, the energy absorber 302 is attached integrally to the collimator A 303 as shown in FIG. 7. To reduce the beam diameter, the energy absorber 302 should preferably be located as downstream as possible to shorten the drift distance of a low-energy beam. Alternatively, the energy absorber 302 may be provided in the form of a flat plate as shown in FIG. 8. In this case, the energy absorber 302 is located more upstream than in the case of FIG. 6 or 7, entailing the disadvantage of an increased beam diameter. Still, the advantage is that the energy absorber 302 is easier to manufacture and that the manufacturing cost of the short-range applicator 101 is lowered.

Figure 9:
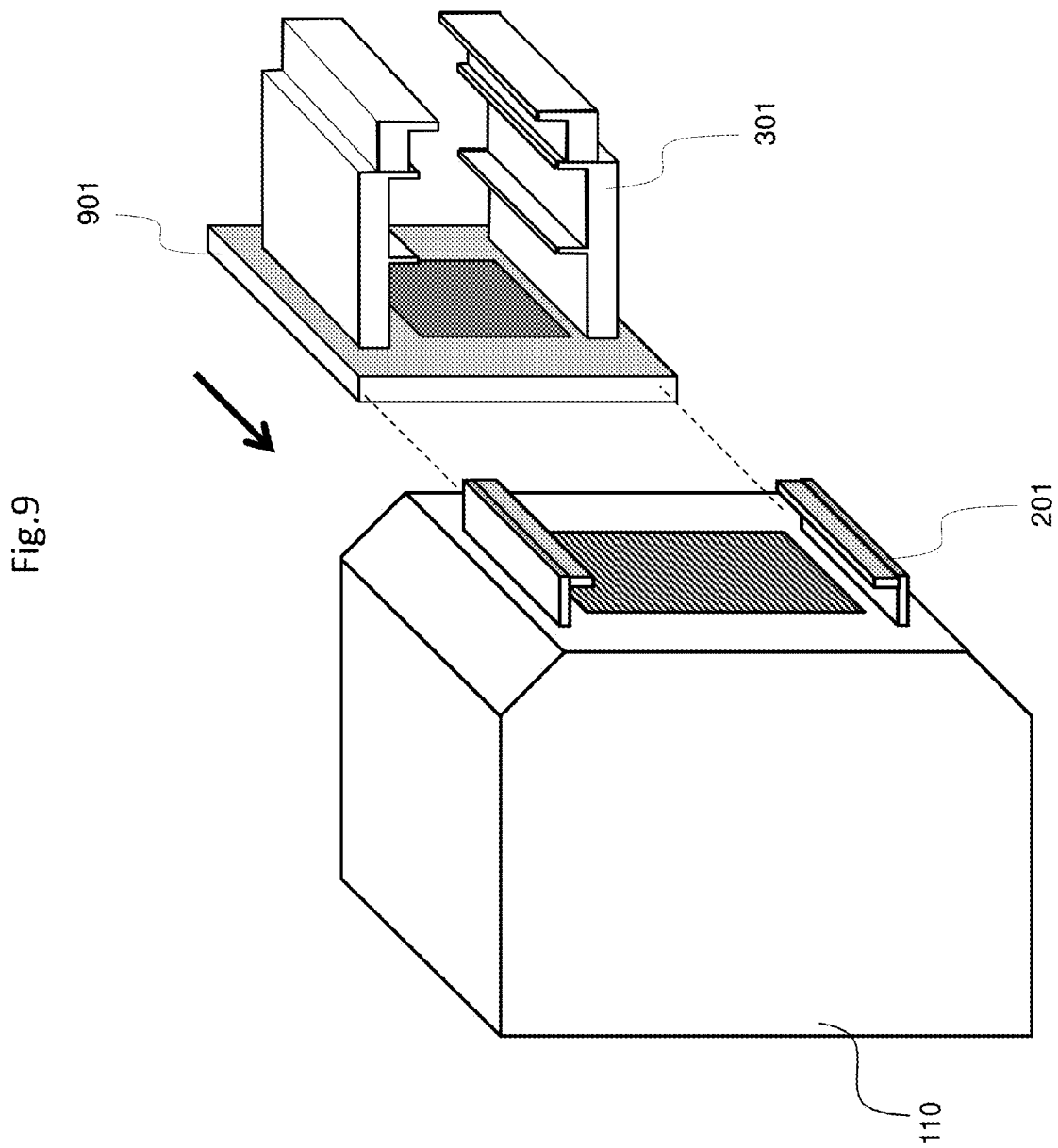
FIG. 9 is a schematic diagram showing one way of attaching the short-range applicator to the irradiation nozzle as part of the embodiment of the invention.
Figure 10:
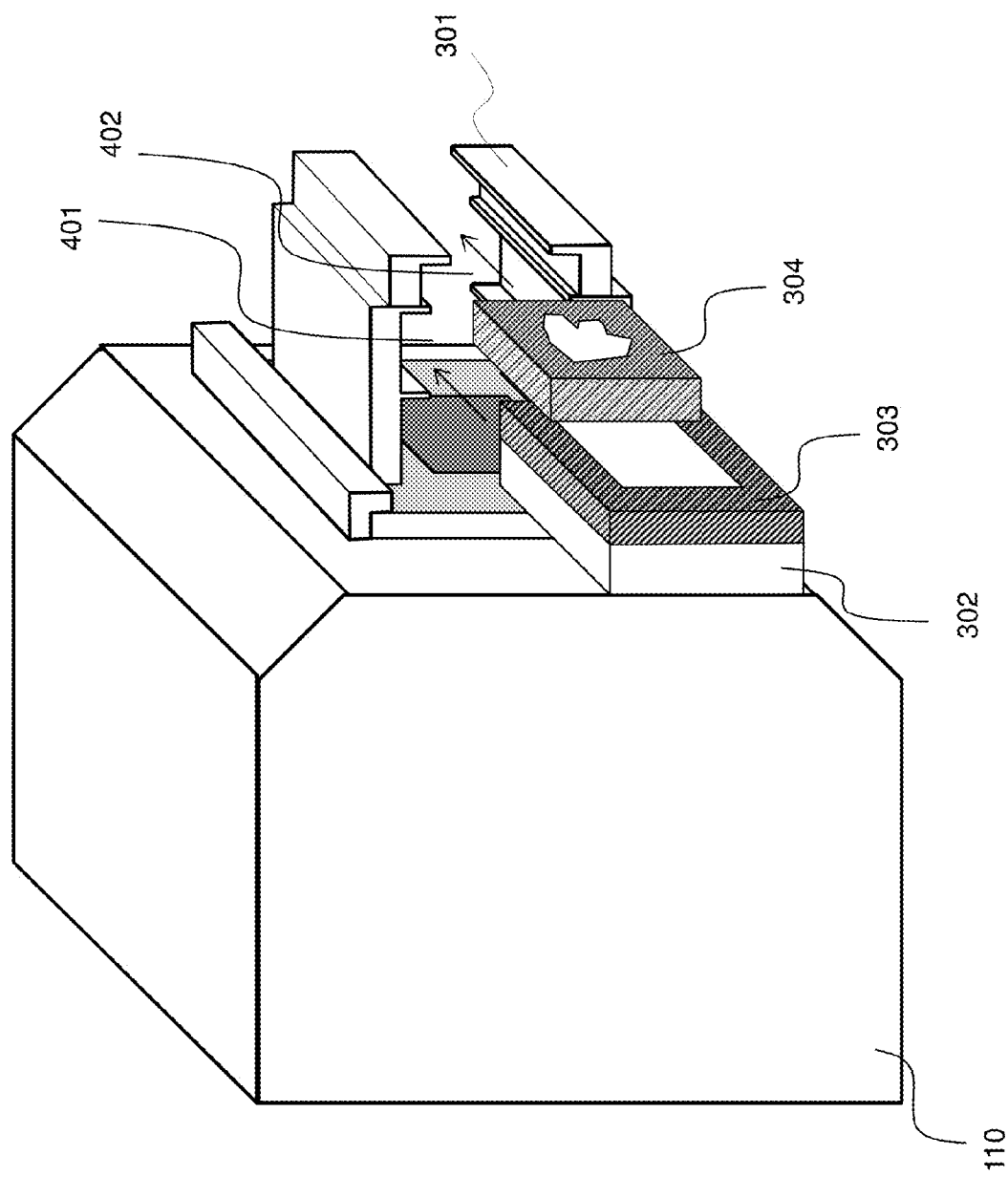
FIG. 10 is a schematic diagram showing another way of attaching the short-range applicator to the irradiation nozzle as part of the embodiment of the invention.

Explained below by use of FIGS. 9 and 10 is the procedure for attaching the short-range applicator 101 to the irradiation nozzle 110. As shown in FIG. 9, a joint part 901 of the support frame 301 is slid laterally into the slot C 201 at the tip of the irradiation nozzle 110, and is fixed with fixtures such as bolts (not shown). At this point, the energy absorber 302 and the collimators A 303 and B 304 are removed from the support frame 301. Then as shown in FIG. 10, the energy absorber 302 integral with the collimator A 303 is slid laterally into the slot A 401 and fixed with fixtures (not shown). Lastly, the collimator B 304 is slid laterally into the slot B 402 and fixed with fixtures (not shown).

For this embodiment, the method and the procedure for installing the short-range applicator 101 are established as described above. However, the same effects can be obtained with some other suitable method as long as it allows the energy absorber 302 and the collimators A 303 and B 304 to be attached securely to the irradiation nozzle 110.

Figure 11:
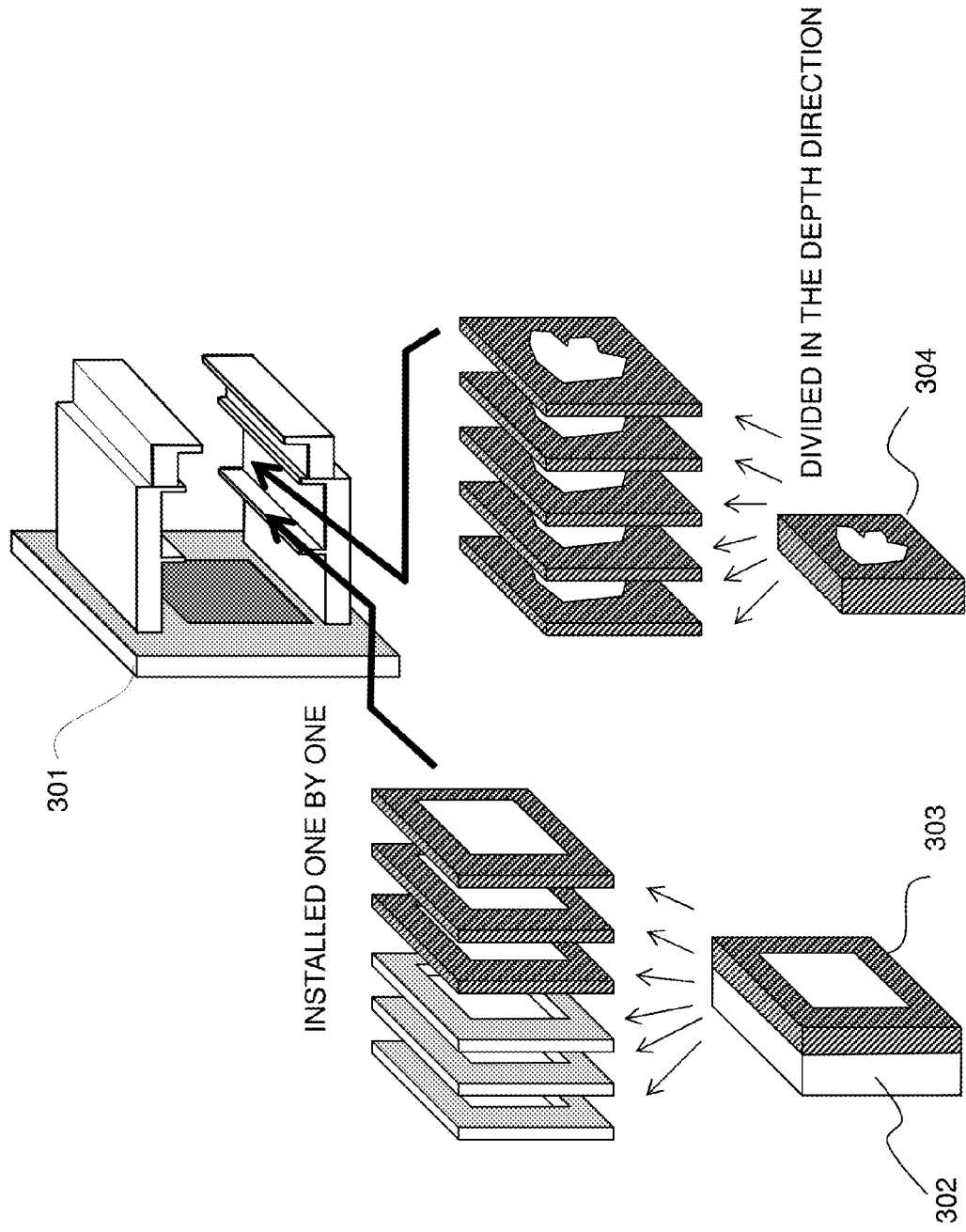
FIG. 11 is a schematic diagram showing another way of attaching the short-range applicator to the irradiation nozzle as part of the embodiment of the invention.

Alternatively, as shown in FIG. 11, the energy absorber 302, collimator A 303, and collimator B 304 may each be divided into multiple parts in the depth direction, each of the parts being attached individually to the support frame 301. This structure also provides the same effects as described above for this embodiment. Because the weight per part is reduced, the burden on the operator is further alleviated when the short-range applicator 101 is set up.

Figure 12:
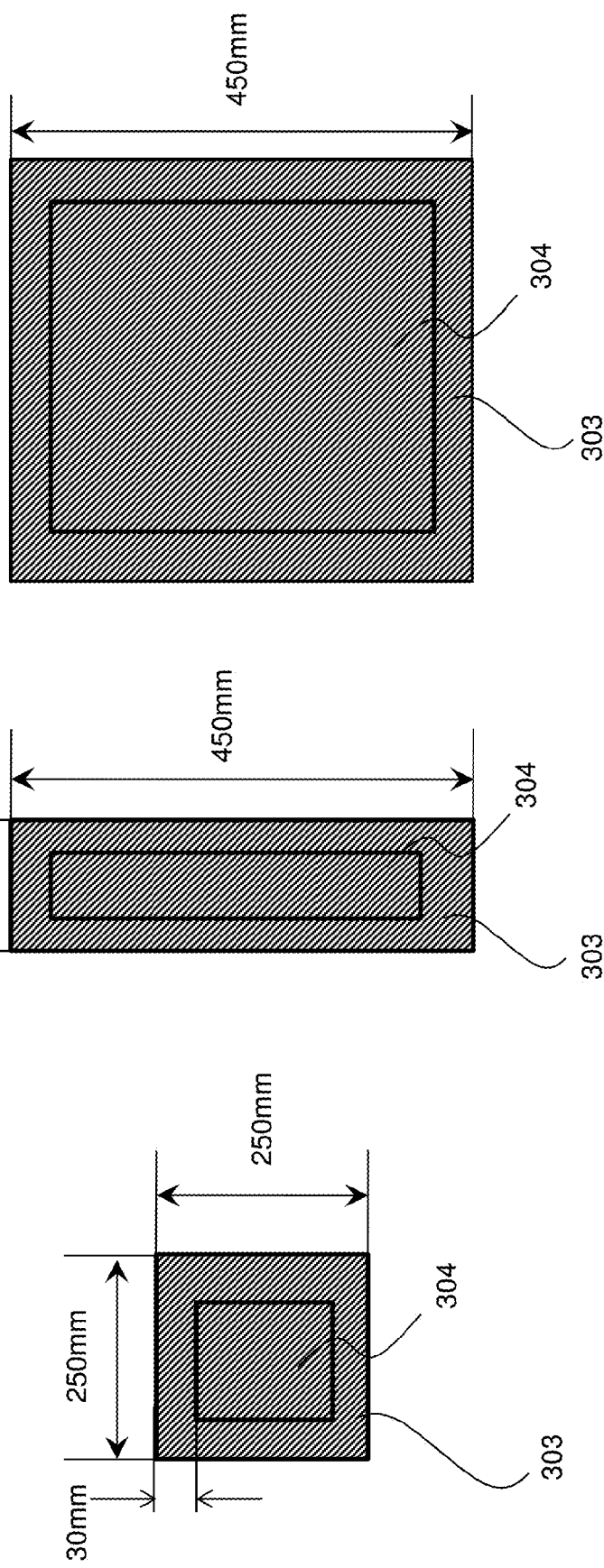
FIG. 12 is a schematic diagram of another collimator A and another collimator B as part of the embodiment of the invention.

The proton beam irradiation apparatus 102 is capable of irradiating the range of 400 mm by 300 mm with the beam on the isocenter plane. It follows that if the general-purpose short-range applicator 101 is adopted for all conceivable irradiation conditions, the energy absorber 302 and the collimators A 303 and B 304 are required to be enlarged. The particle therapy system of this embodiment thus adopts a short-range applicator 101 of a dedicated shape for each treated area (e.g., head and neck area, spine, etc.) as shown in FIG. 12. The shape of the irradiation field required in radiation treatment is more or less predetermined for each treated area. Thus if the short-range applicator 101 is designed with a dedicated shape for each treated area, the short-range applicator 101 can be reduced to a size necessary and sufficient for each treatment. Thus further alleviates the burden on the operator when the short-range applicator 101 is set up.

Figure 13:
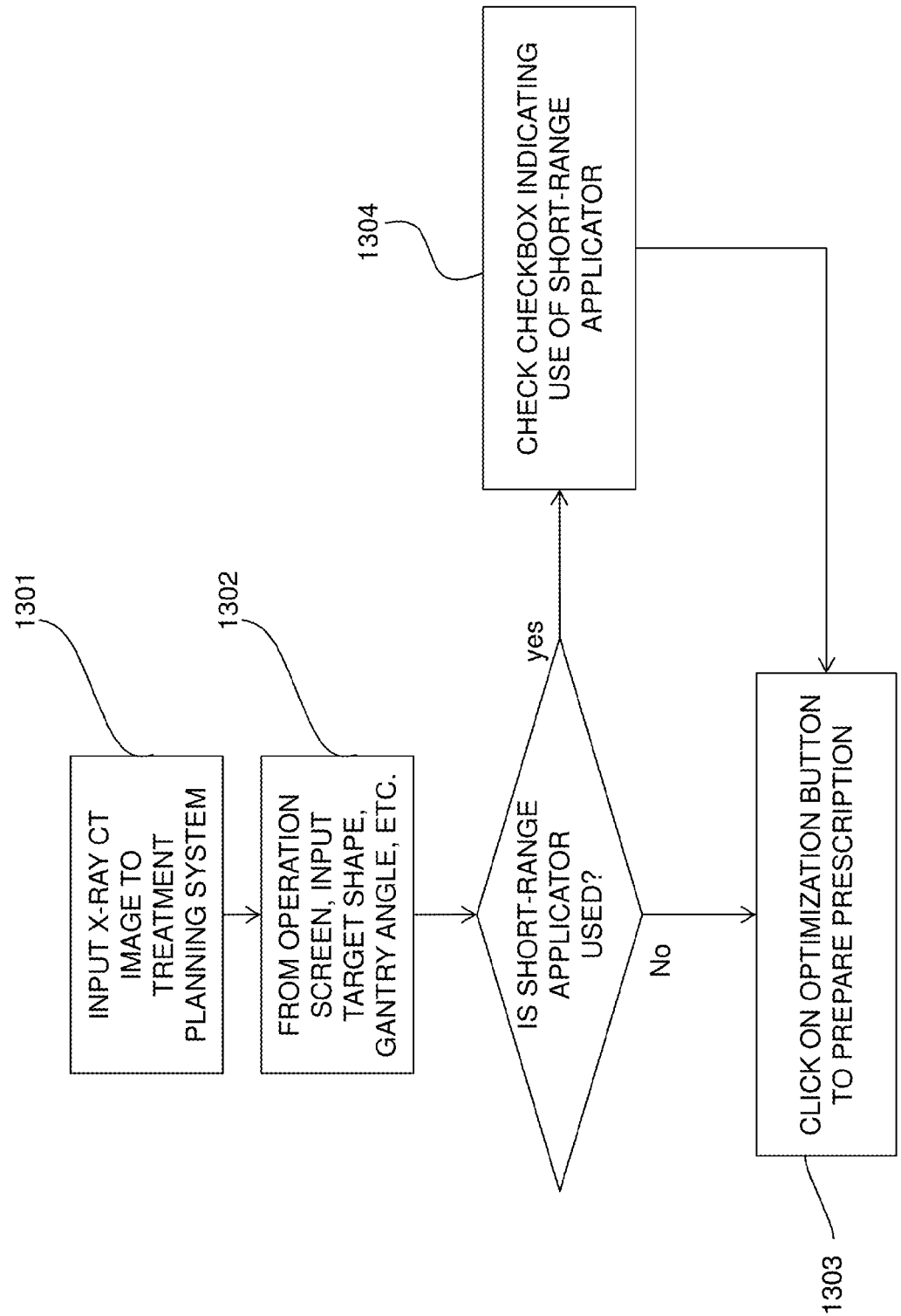
FIG. 13 is a flowchart showing a treatment planning procedure for use with the embodiment of the invention.
Figure 14:
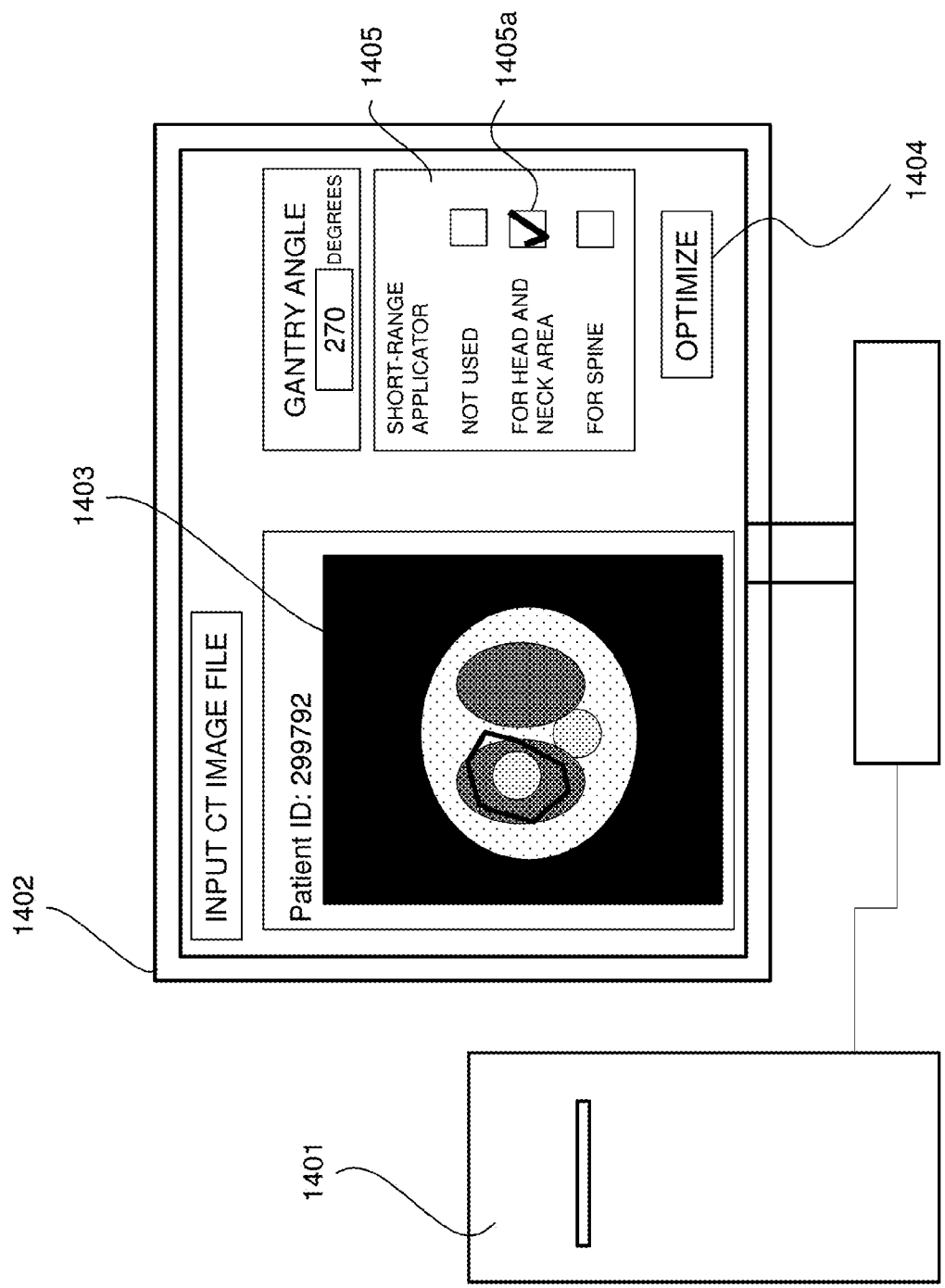
FIG. 14 is a schematic diagram of a treatment planning system as part of the embodiment of the invention.

The treatment planning procedure in effect when the short-range applicator 101 is used is explained below by use of the treatment planning flowchart in FIG. 13 and the schematic diagram of the treatment planning system in FIG. 14 as part of the particle treatment system embodying the present invention. As shown in FIG. 14, the treatment planning system 1401 displays an operation screen 1402 for selecting the use or non-use of the short-range applicator 101 and the type of the short-range applicator 101 to be used. The treatment planning system 1401 records to a prescription the use or non-use of the short-range applicator 101 selected on the displayed operation screen 1402, and the type of the short-range applicator 101 selected to be used on the screen 1402, and outputs the prescription to an irradiation controller 1503 (see FIG. 15). Also, where the short-range applicator 101 is used, the treatment planning system 1401 limits the arrangement of usable spots and a usable beam extracted from the proton beam generator 103 to a range corresponding to the short-range applicator 101 to be used at the time of optimized calculation. Furthermore, the treatment planning system 1401 records for each treated area the information about the short-range applicator 101 of the dedicated shape, the use or non-use of the short-range applicator 101 selected on the operation screen 1402, and the type of the short-range applicator 101 also selected to be used on the screen 1402.

The operator first inputs X-ray CT image information about the irradiated body to the treatment planning system 1401 for display on the operation screen 1402 (step 1301).

Then while verifying a CT image on the operation screen 1402, the operator designates the direction of irradiation (i.e., angle of the rotating gantry) and the range of the target by use of a user interface (e.g., mouse, not shown)(step 1302). Although the X-ray CT image information is used for this embodiment, the same effects can be obtained with any image that allows the internal structure of the irradiated body to be verified.

Where the short-range applicator 101 is not used, the operator clicks on an optimization button 1404 on the operation screen 1402. This causes the treatment planning system to calculate a suitable arrangement of steps allowing the designated target to be irradiated uniformly with a sufficient dose, the beam energy for irradiation of each spot, and the amount of beam irradiation, and to output the results of the calculations as the prescription (step 1303).

On the other hand, where the short-range applicator 101 is used, the operator checks a checkbox 1405 for the use of the relevant short-range applicator on the operation screen 1402 (step 1304). For example, if the operator checks a checkbox 1405a for a short-range applicator used for the head and neck area and having a collimator A 250 mm by 250 mm in width, the treatment planning system 1401 limits the arrangement of usable spots to within 200 mm by 200 mm at the time of optimized calculation in preparation of the prescription. Also at the time of optimized calculation, a usable beam extracted from the proton beam generator 103 is limited to a range of less than 100 mm. Later, when the optimization button 1404 is clicked on, the treatment planning system 1401 outputs the prescription that limits the arrangement of spots to within 200 mm by 200 mm and the beam range to within 100 mm (step 1303). The prescription also carries information about the type of the short-range applicator (e.g., head and neck area, spine, etc.).

The treatment planning system 1401 of this embodiment thus possesses the function of preventing accidental irradiation when the short-range applicator 101 is set up. As described above, the short-range applicator 101 of this embodiment has a dedicated shape for each treated area in order to be small in size. However, because the proton beam irradiation apparatus 102 is capable of beam irradiation in the range of 400 mm by 300 mm on the isocenter plane, the function of preventing inadvertent beam irradiation outside the collimator A 303 is mandatory. Although this embodiment limits the arrangement of spots to within 200 mm by 200 mm for the short-range applicator 250 mm by 250 mm in width, the constraints on the spot arrangement may need to be altered depending on the beam diameter and the criteria for the amount of beam leakage.

In this embodiment, the collimators A 303 and B 304 are each set to be 20 mm in thickness. The proton beam irradiation apparatus 102 is capable of emitting the beam in the range of up to 300 mm, the emitted beam being powerful enough to pass through the collimator thickness with ease. It follows that the function of preventing the accidental emission of a high-energy beam (i.e., long-range beam) mainly attributable to the operator's mistake is mandatory, as in this embodiment. Although this embodiment limits the range of beam irradiation to within 100 mm, the constraints on the range of beam irradiation may need to be altered depending on the thickness of the energy absorber 302 and on the thickness of the collimators A 303 and B 304.

In this embodiment, the proton beam irradiation apparatus 102 and short-range applicator 101 are also equipped with an interlock mechanism for preventing accidental irradiation. As shown in the block diagram of FIG. 15, the slot C 201 at the tip of the irradiation nozzle 110 is equipped with a sensor 1501, and a connecting part 901 of the support frame 301 is furnished with an IC chip (first sensor) 1502. The IC chip 1502 records information about the type of the short-range applicator 101 (e.g., for head and neck area, spine, etc.). When the support frame 301 is connected to the irradiation nozzle 110 in accordance with the above-described procedure, the sensor 1501 reads the information from the IC chip 1502 and sends the retrieved information to the irradiation controller 1503. Meanwhile, the slots A 401 and B 402 are equipped with limit switches (second sensors) 1504 that monitor the status of the energy absorber 302 and the collimators A 303 and B 304 being attached or detached. Only when the energy absorber 302 and the collimators A 303 and B 304 have been correctly attached to the support frame 302, do the limit switches 1504 output signals to the irradiation controller 1503 via the sensor 1501.

FIG. 16 is a flowchart showing the workings of the above-described interlock mechanism. To emit the beam to the irradiated body, the operator first performs operations to input the prescription from the treatment planning system 1401 to the irradiation controller 1503 (step 1601). In turn, the irradiation controller 1503 reads from the prescription the use or non-use of the short-range applicator 101 for the current beam irradiation and the type of the short-range applicator 101 to be used. Furthermore, the irradiation controller 1503 compares the retrieved information and the information in the IC chip 1502 output from the sensor 1501 of the irradiation nozzle 110 (step 1602). Following the verification that the same short-range applicator 101 as that noted in the prescription is attached to the irradiation nozzle 110, the irradiation controller 1503 checks whether all limit switches 1504 output their signals (step 1603). After the verification that all limit switches 1504 output the signals, the irradiation controller 1503 transmits a beam irradiation start permission signal to the proton beam irradiation apparatus 102 (step 1604). Although the IC chip 1502 and sensor 1501 are used in this embodiment, the same effects can be obtained with some other suitable method as long as it allows the type of the short-range applicator 101 to be identified. And whereas the limit switches 1504 are used in this embodiment, the same effects can be acquired with some other suitable method as long as it permits monitoring of the status of each relevant device being attached or detached.

Explained below is the procedure for irradiating the short-range region with the beam by use of the particle therapy system of this embodiment. First, the irradiated body is secured to a patient's couch (not shown) provided in the treatment room (not shown). The patient's couch can be moved in six-axis directions, allowing the operator to shift the irradiated body to a desired position. Next, a laser marker (not shown) and an X-ray imaging device (not shown) attached to the rotating gantry are used to calculate the amount of deviation between the current position of the irradiated body and the position designated by the treatment plan in effect. The patient's couch is moved sufficiently to minimize the amount of deviation. Further, the short-range applicator 101 is attached to the irradiation nozzle 110 in accordance with the above-described procedure, and the rotating gantry is rotated to the same angle as that designated in the treatment plan. Following the above-described work in the treatment room, the operator goes to an irradiation control room (not shown). Finally, the operator inputs to the irradiation controller 1503 the prescription prepared beforehand by use of the treatment planning system 1401, and starts beam irradiation. After the verification that the short-range applicator 101 is correctly attached to the irradiation nozzle 110, the irradiation controller 1503 transmits a beam irradiation permission signal to the proton beam irradiation apparatus 102. Upon receipt of the beam irradiation permission signal, the proton beam irradiation apparatus 102 irradiates each of the spots successively with the beam in accordance with the above-described procedure of the scanning method and on the basis of the information described in the prescription.

As described above, the present invention provides a particle therapy system equipped with an irradiation nozzle that forms the irradiation field using the scanning method in a manner improving the penumbrae in the short-range region without hiking costs, increasing the penumbrae outside the short-range region, or increasing the burden on the operator. Because the use of the short-range applicator increases the width of the Bragg peak, there are fewer spots in the depth direction needed to form an expanded Bragg peak, which enhances the dose rate. Furthermore, the expanded Bragg peak improves the robustness of intra-target dose uniformity.

It should be understood that the present invention when embodied is not limited to the above-described embodiments and that various modifications, variations and alternatives may be made of the invention.

DESCRIPTION OF REFERENCE CHARACTERS

101: Irradiation compensating device (short-range applicator)
102: Proton beam irradiation apparatus
103: Proton beam generator
104: Proton beam transfer
105: Rotating irradiation system
106: Ion source
107: Preaccelerator
108: Synchrotron
109: Extraction deflector
110: Irradiation nozzle
201: Slot C
301: Support frame
302: Energy absorber
303: Collimator A
304: Collimator B
401: Slot A
402: Slot B
501: Aperture of collimator A
502: Aperture of collimator B
601: Central protrusion of energy absorber
901: Joint part of support frame
1301: Treatment planning step
1302: Treatment planning step
1303: Treatment planning step
1304: Treatment planning step
1401: Treatment planning system
1402: Operation screen
1403: X-ray CT image of irradiated body
1404: Optimization button
1405: Checkbox indicating use or non-use of short-range applicator
1405a: Checkbox indicating type of short-range applicator to be used
1501: Sensor
1502: IC chip
1503: Irradiation controller
1504: Limit switches
1601: Step preparatory to beam irradiation
1602: Step preparatory to beam irradiation
1603: Step preparatory to beam irradiation
1604: Step preparatory to beam irradiation

The invention claimed is:

1. A particle therapy system comprising:
an irradiation nozzle forming an irradiation field using a scanning method;
an irradiation compensating device used in a short-range region, the irradiation compensating device including a frame, an energy absorber, a first collimator, a second collimator, and the energy absorber, the first collimator, and the second collimator are individually attachable to and detachable from the support frame, and the support frame of the irradiation compensating device is attachable to and detachable from the irradiation nozzle; and
a treatment planning system configured to:
select use or non-use of the irradiation compensating device and a type of the irradiation compensating device to be used at a time of optimized calculation in preparation of a prescription,
record to the prescription the selected use or non-use of the irradiation compensating device and the selected type of the irradiation compensating device to be used, and
output the prescription.

2. The particle therapy system according to claim 1, wherein:
in the irradiation compensating device, lateral shapes of the energy absorber, the first collimator, and the second collimator are grouped into at least two types.

3. The particle therapy system according to claim 2, wherein:
when the use of the irradiation compensating device is selected, the treatment planning system limits, for the selected irradiation compensating device in performing the optimized calculation, a range in which spots can be arranged and an energy of a usable extracted beam.

4. The particle therapy system according to claim 3, further comprising:
a proton beam irradiation apparatus and an irradiation controller, wherein:
the irradiation nozzle has a first sensor that monitors a status of the irradiation compensating device being attached or detached thereto and monitors the type of the irradiation compensating device, the first sensor outputting a monitored result to the irradiation controller,
when the prescription output from the treatment planning system is input to the irradiation controller, the irradiation controller is configured to:
compare first information recorded in the input prescription and second information output from the first sensor, the first information including whether the use or non-use of the irradiation compensating device is selected at the time of the optimized calculation and the selected type of the irradiation compensating device, and the second information including a status of the irradiation compensating device being attached to or detached from the irradiation nozzle and the type of the attached irradiation compensating device, and
permit the proton beam irradiation apparatus to emit a beam only when the first and second information match each other.

5. The particle therapy system according to claim 4, wherein:
the irradiation compensating device has a plurality of second sensors that monitor statuses of the energy absorber, the first collimator, and the second collimator being attached or detached thereto, the second sensors outputting a monitored result to the irradiation controller, and
the irradiation controller permits the proton beam irradiation apparatus to emit the beam only when:

the use of the irradiation compensating device is recorded in the prescription, and all of the energy absorber, the first collimator, and the second collimator are found to be attached to the irradiation compensating device on the basis of the information output from the second sensors.

6. The particle therapy system according to claim 1, wherein:

when the use of the irradiation compensating device is selected, the treatment planning system is configured to:

limit, for the selected type irradiation compensating device in performing optimized calculation, a range in which spots can be arranged and an energy of a usable extracted beam.

7. The particle therapy system according to claim 1, further comprising:

a proton beam irradiation apparatus and an irradiation controller, wherein:

the irradiation nozzle has a first sensor that monitors a status of the irradiation compensating device being attached or detached to the frame and monitors the type of the irradiation compensating device, the first sensor outputting a monitored result to the irradiation controller, when the prescription output from the treatment planning system is input to the irradiation controller, the irradiation controller is configured to:

compare first information recorded in the input prescription and second information output from the first sensor, the first information including whether the use or non-use of the irradiation compensating device is selected at the time of the optimized calculation and the selected type of the irradiation compensating device, and the second information including a status of the irradiation compensating device being attached to or detached from the irradiation nozzle and the type of the attached irradiation compensating device, and permit the proton beam irradiation apparatus to emit a beam only when the first and second information match each other.

8. The particle therapy system according to claim 7, wherein:

the irradiation compensating device has a plurality of second sensors that monitor statuses of the energy absorber, the first collimator, and the second collimator being attached or detached to the frame, the second sensors outputting the monitored result to the irradiation controller, and the irradiation controller permits the proton beam irradiation apparatus to emit the beam only when:

the use of the irradiation compensating device is recorded in the prescription, and all of the energy absorber, the first collimator, and the second collimator are found to be attached to the irradiation compensating device on the basis of the information output from the second sensors.

9. The particle therapy system according to claim 1, wherein:

each of the energy absorber, the first collimator, and the second collimator are divided into multiple parts which are separately attachable to and detachable from the support frame.

10. A particle therapy system comprising:

an irradiation nozzle forming an irradiation field using a scanning method;

an irradiation compensating device used in a short-range region, the irradiation compensating device including a frame, an energy absorber, a first collimator, a second collimator, and the energy absorber, the first collimator, and the second collimator are individually attachable to and detachable from the support frame, and the support frame of the irradiation compensating device is attachable to and detachable from the irradiation nozzle;

a treatment planning system configured to:

select use or non-use of the irradiation compensating device and a type of the irradiation compensating device to be used at a time of optimized calculation in preparation of a prescription, record to the prescription the selected use or non-use of the irradiation compensating device and the selected type of the irradiation compensating device to be used, and output the prescription; and a proton beam irradiation apparatus and an irradiation controller, wherein:

the irradiation nozzle has a first sensor that monitors a status of the irradiation compensating device being attached or detached thereto and monitors the type of the irradiation compensating device, the first sensor outputting a monitored result to an irradiation controller, and when the prescription output from the treatment planning system is input to the irradiation controller, the irradiation controller configured to:

compare first information recorded in the input prescription and second information output from the first sensor, the first information including whether the use or non-use of the irradiation compensating device is selected at the time of the optimized calculation and the type of the irradiation compensating device, and the second information including a status of the irradiation compensating device being attached to or detached from the irradiation nozzle and the type of the attached irradiation compensating device, and permit the proton beam irradiation apparatus to emit a beam only when the first and second information match each other.

11. The particle therapy system according to claim 10, wherein:

the irradiation compensating device has a plurality of second sensors that monitor statuses of the energy absorber, the first collimator, and the second collimator being attached or detached to the frame, the second sensors outputting a monitored result to the irradiation controller, and the irradiation controller permits the proton beam irradiation apparatus to emit the beam only when:

the use of the irradiation compensating device is recorded in the prescription, and all of the energy absorber, the first collimator, and the second collimator are found to be attached to the irradiation compensating device on the basis of the information output from the second sensors.

12. The particle therapy system according to claim 10, wherein:

each of the energy absorber, the first collimator, and the second collimator are divided into multiple parts which are separately attachable to and detachable from the support frame.

* * * * *